United States Patent
Ryall et al.

(10) Patent No.: US 9,173,663 B2
(45) Date of Patent: Nov. 3, 2015

(54) ADAPTER FOR A SURGICAL REAMER DRIVER

(71) Applicant: Symmetry Medical, Inc., Warsaw, IN (US)

(72) Inventors: Clive Ryall, Oakland Parks (GB); Julian Ferreira, Tewkesbury (GB)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 358 days.

(21) Appl. No.: 13/892,613

(22) Filed: May 13, 2013

(65) Prior Publication Data

US 2013/0253520 A1   Sep. 26, 2013

Related U.S. Application Data

(63) Continuation of application No. 12/237,537, filed on Sep. 25, 2008, now Pat. No. 8,439,920.

(60) Provisional application No. 60/974,882, filed on Sep. 25, 2007.

(51) Int. Cl.
*A61B 17/16* (2006.01)

(52) U.S. Cl.
CPC ......... *A61B 17/1631* (2013.01); *A61B 17/1666* (2013.01); *A61B 17/1617* (2013.01)

(58) Field of Classification Search
None
See application file for complete search history.

(56) References Cited

U.S. PATENT DOCUMENTS

| | | | |
|---|---|---|---|
| 3,702,611 A | 11/1972 | Fishbein | |
| 4,023,572 A * | 5/1977 | Weigand et al. | 606/81 |
| 4,751,922 A | 6/1988 | DiPietropolo | |
| 5,553,675 A | 9/1996 | Pitzen et al. | |
| 5,658,290 A | 8/1997 | Lechot | |
| 5,817,096 A | 10/1998 | Salyer | |
| 5,980,170 A | 11/1999 | Salyer | |
| 6,126,359 A | 10/2000 | Dittrich et al. | |
| 6,258,107 B1 | 7/2001 | Balazs et al. | |
| 6,283,972 B1 * | 9/2001 | Riley | 606/81 |
| 6,854,742 B2 | 2/2005 | Salyer et al. | |
| 7,115,119 B2 | 10/2006 | Desarzens | |
| 7,229,078 B2 | 6/2007 | Lechot | |
| 7,326,198 B2 | 2/2008 | Desarzens et al. | |
| 2003/0216716 A1 | 11/2003 | Desarzens | |
| 2004/0049199 A1 * | 3/2004 | Lechot et al. | 606/80 |
| 2007/0191854 A1 | 8/2007 | Grim | |
| 2007/0203477 A1 | 8/2007 | Lechot | |

* cited by examiner

*Primary Examiner* — David Bates
*Assistant Examiner* — Samuel Hanna
(74) *Attorney, Agent, or Firm* — Taylor IP, P.C.

(57) ABSTRACT

An adapter for a surgical reamer driver having one of a crossbar and a crossbridge reamer driver. The adapter includes a base having an interface for connecting with one of the crossbar and crossbridge reamer drivers. The adapter further includes at least one recess on the opposite end of the base opening in an axial direction. The recess is configured to receive a reamer of a style unlike the given style interface. A pair of hooks or tabs resiliently hold the reamer in place in the recesses.

1 Claim, 4 Drawing Sheets

ADAPTER FOR A SURGICAL REAMER DRIVER

CROSS REFERENCE TO RELATED APPLICATIONS

This is a continuation of U.S. patent application Ser. No. 12/237,537, entitled "ADAPTER FOR A SURGICAL REAMER DRIVER", filed Sep. 25, 2008 which is based upon U.S. provisional patent application Ser. No. 60/974,882, entitled "ADAPTER FOR ORTHOPAEDIC REAMER", filed Sep. 25, 2007, which is incorporated herein by reference.

BACKGROUND OF THE INVENTION

1. Field of the Invention

The present invention relates to orthopedic surgical reamers and more specifically to drivers for such tools.

In the field of orthopaedic surgery, it is often necessary to remove bone material to enable implantation of prosthesis to repair joints in the human body. Patella cutters and acetabular reamer cups and glenoid reamers are surgical tools which are used in surgery for the insertion of artificial joints. Acetabular reamer cups are used to cut hemispherical cavities in pelvis bones for the insertion of artificial hip joints. Patella cutters are used to shape the underside of the patella or knee cap during knee replacement surgery. Glenoid reamers are used to cut hemispherical cavities in shoulder bones for the insertion of artificial shoulder joints. Patella cutters have a complex arrangement of precisely shaped cutting edges arranged around an axis of rotation for cutting the patella. Acetabular reamer cups and glenoid reamers have a complex arrangement of cutting edges arranged on a spherical surface around the axis of rotation of the cup.

A number of tools have been developed for this purpose and include reamers having generally semi-hemispherical configuration with cutting elements on them so that a corresponding semi-hemispherical hollow can be formed in the bone material for providing a foundation for the repair of the joint.

There are two major driver styles in the field, one of which is for the Othy style manufactured by Symmetry Medical, Inc. and the other style manufactured by Precimed SA of L'Echelette, Switzerland. Although these both have semi-hemispherical cutting heads, they have different interfaces between driving tools with which they are associated. The Othy style has a crossbridge element. This element is a bar extending between the circumference of the hemisphere and having a circular expanded section in the middle. Numerous arrangements are available for securing this device as exemplified by U.S. Pat. No. 6,854,742. Alternatively, the Precimed reamer has a crossbar shape in which two circular cross section bars intersect at the center and extend to the walls of the hemisphere. An example of a driver for this type is found in U.S. Pat. No. 5,658,290 in which a bayonet interconnection is provided between the reamer and the driver.

Typically, surgeons use specialized drivers for each of the reamers. The drivers connect to a source of power and have appropriate handles for guiding the operation of the reamer by a surgeon. If a surgeon has one of the adaptors, it is difficult to utilize the other type of reamer since it requires a specialized driver for that reamer. It has been proposed in U.S. Pat. No. 7,115,119 to provide a dual adapter that accommodates both the Othy and the Precimed reamers. However, this style of dual reamer requires investment in a new reamer driver assembly to connect with the two different styles. In addition, this type of driver has a bayonet interconnection in which the assemblies are inserted axially and then a rotational movement, in accordance with a bayonet connection, is provided to lock the elements in place. This type of action slows the process of utilizing a new reamer because of the additional movement, But, more than that, the release of the device, after it has been in the surgical environment, is more difficult because it requires holding the reamer to reverse the rotational movement and then axial movement to finally free the reamer.

What is needed in the art, therefore, is an adapter for surgical reamers that enables rapid and immediate connection and disconnection of the reamers.

SUMMARY OF THE INVENTION

In one form, the invention is an adapter for a surgical reamer driver having a given style interface for connection with a given style reamer. The adapter includes a base having an interface on one end configured to mate with said given interface. At least one recess on the opposite end of the base opens in an axial direction and is configured to releasably receive a reamer of a style unlike the given style interface.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate one embodiment of the invention, in one form, and such exemplifications are not to be construed as limiting the scope of the invention in any manner.

DETAILED DESCRIPTION OF THE INVENTION

Figure 1:
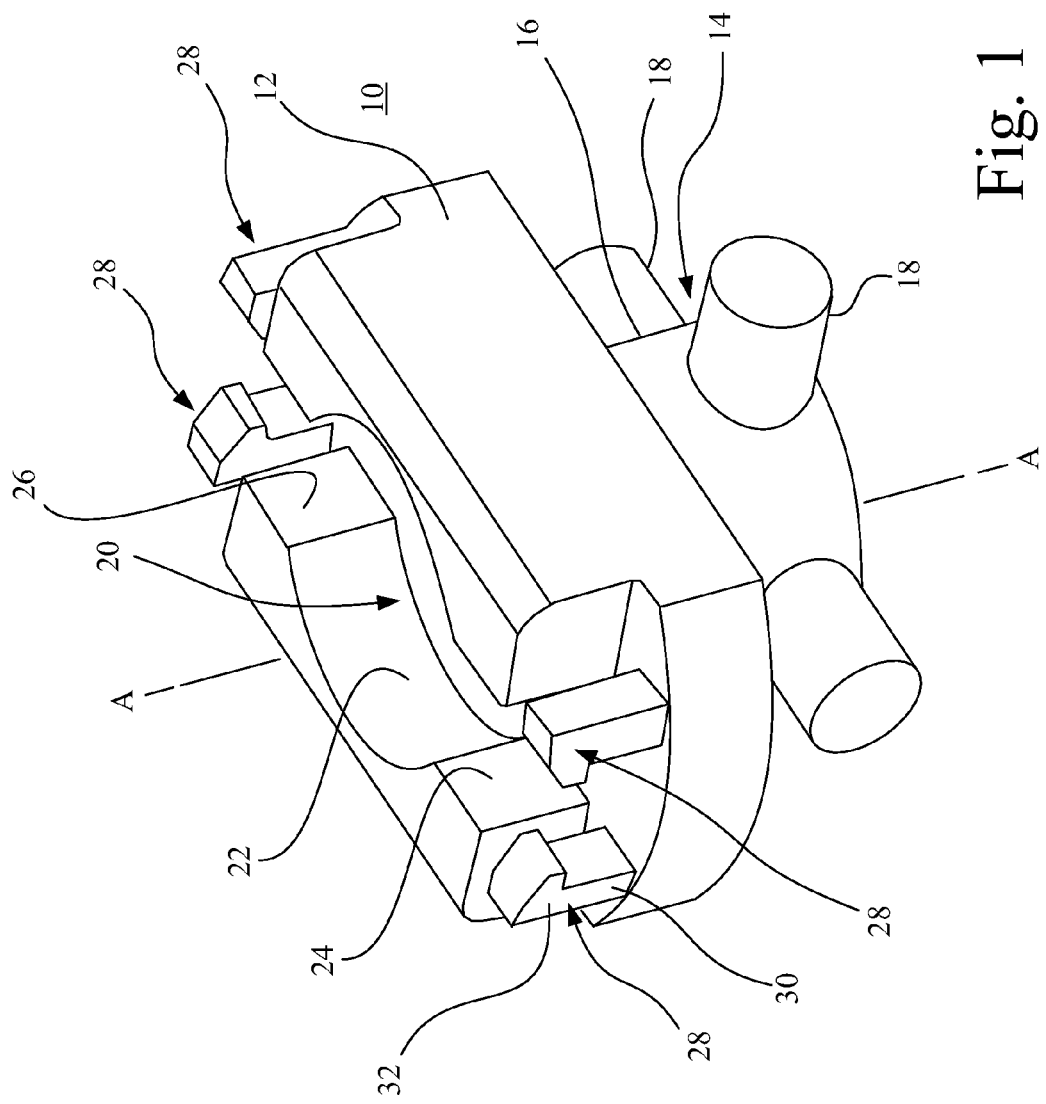
FIG. 1 shows a perspective view of an adapter for a reamer driver.
Figure 2:
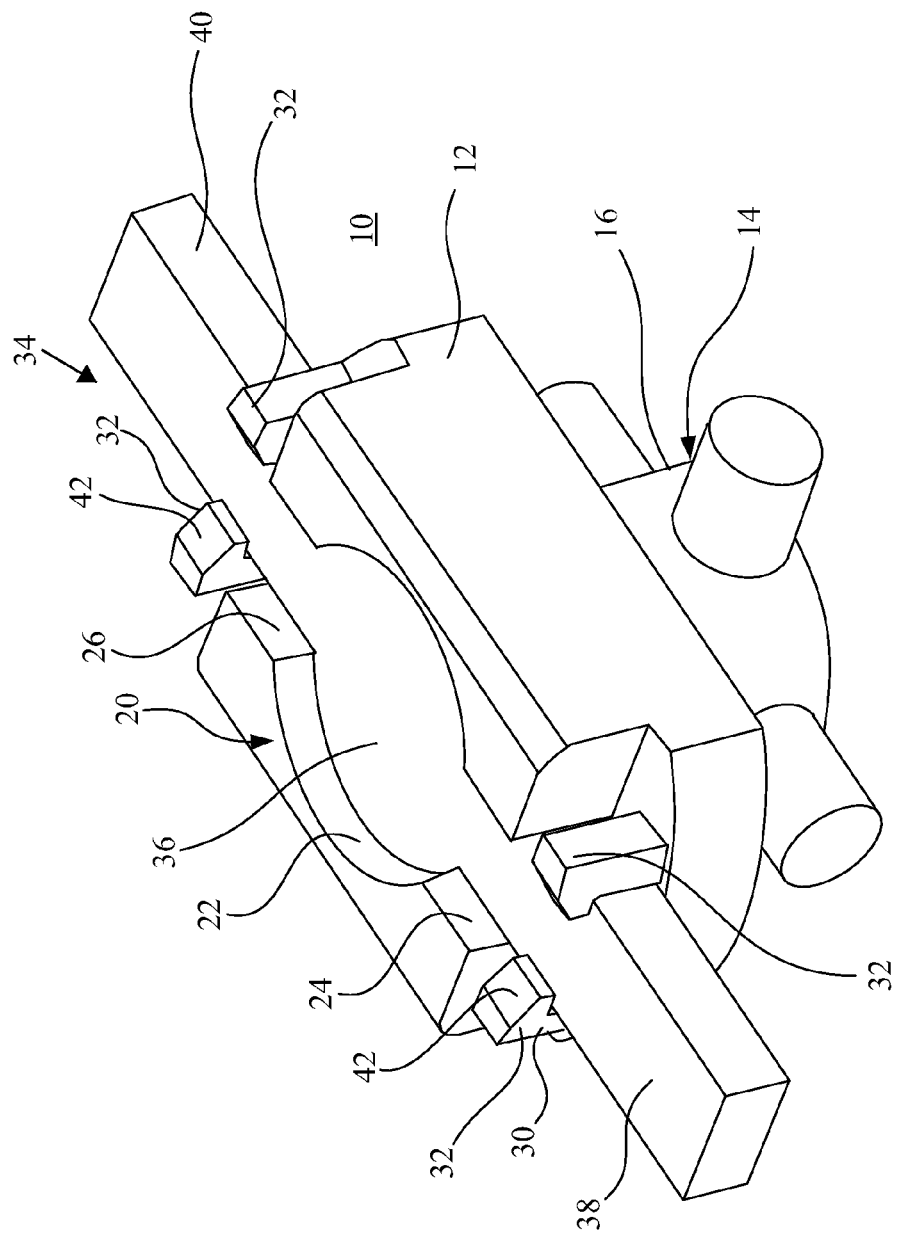
FIG. 2 shows a crossbridge reamer in place in the adapter.

Referring to FIGS. 1 and 2, there is shown one embodiment of an adapter embodying the present invention. The adapter 10 includes a base 12 and having an interface 14 for connecting with a reamer driver (not shown) that is of the crossbar type referred to above. Interface 14 has a central circular section 16 coaxial with a central axis A of the adapter 10. Central circular section 16 has a plurality of circular bars or rods 18 extending radially outward and placed 90° from one another. The interface 14 is configured to connect to the Precimed style of reamer driver that accepts the crossbars represented by the radial elements 18. The base 12 also has a recess 20 at its opposite end to accept a reamer that is different from the reamer configured to accept interface 14.

In the case shown in FIG. 1, the recess 20 is configured for a crossbar reamer manufactured and sold by Symmetry Medical. Recess 20 has a central circular section 22 having a central axis coaxial with the axis A of adapter 10 and a pair of recesses 24 and 26 aligned with one another and extending radially from the central circular section 22. A plurality of hook elements 28 are positioned in line with the radially extending recesses 24 and 26. The hook elements 28 each comprise a base 30 and a lip 32 for capturing an element as described below. Preferably adapter 10 is made from surgically compatible flexible material and molded as a unitary piece. However, it should be apparent to those skilled in the art that the adapter 10 may be formed from a plurality of elements.

As shown in FIG. 2, a crossbar reamer 34 is received in adapter 10. As stated previously, crossbar reamer 34 connects with the interior surface of a semi hemispherical element having cutting edges on it. The hemispherical portion and cutting elements have been omitted to simply an understanding of the invention. The crossbridge reamer 34 has a circular center section 36 received in the circular section 22 and a pair of radially extending rectangular bars 38 and 40, which are received in radially extending recesses 24 and 26, respectively. The crossbridge reamer 34 is held within the adapter 10 by the lip elements 32. The crossbridge reamer 34 is inserted into the recess 20 because the upper portion of lip 32 is angled at 42 to allow camming of the lips 32 outward by virtue of the yieldability of elements 28 to deflect sufficiently to permit entry of the crossbridge element 34 and permit the lips 32 to come back into place and hold it.

The adapter 10 enables a surgeon with a reamer driver designed to connect with a Precimed style reamer to use adapter 10 in interconnecting with a Othy crossbridge style reamer. Since the adapter 10 is made from a unitary material, easily cast and inexpensive to produce, the adapter 10 could either be used as a permanent adapter for the crossbridge element 34 or it could be disposed of after surgical procedures to avoid the cost of additional sterilization. It is to be noted that the material selected for adapter 10 should be capable of temperature exposure of a level commonly found during sterilization of surgical elements.

Figure 3:
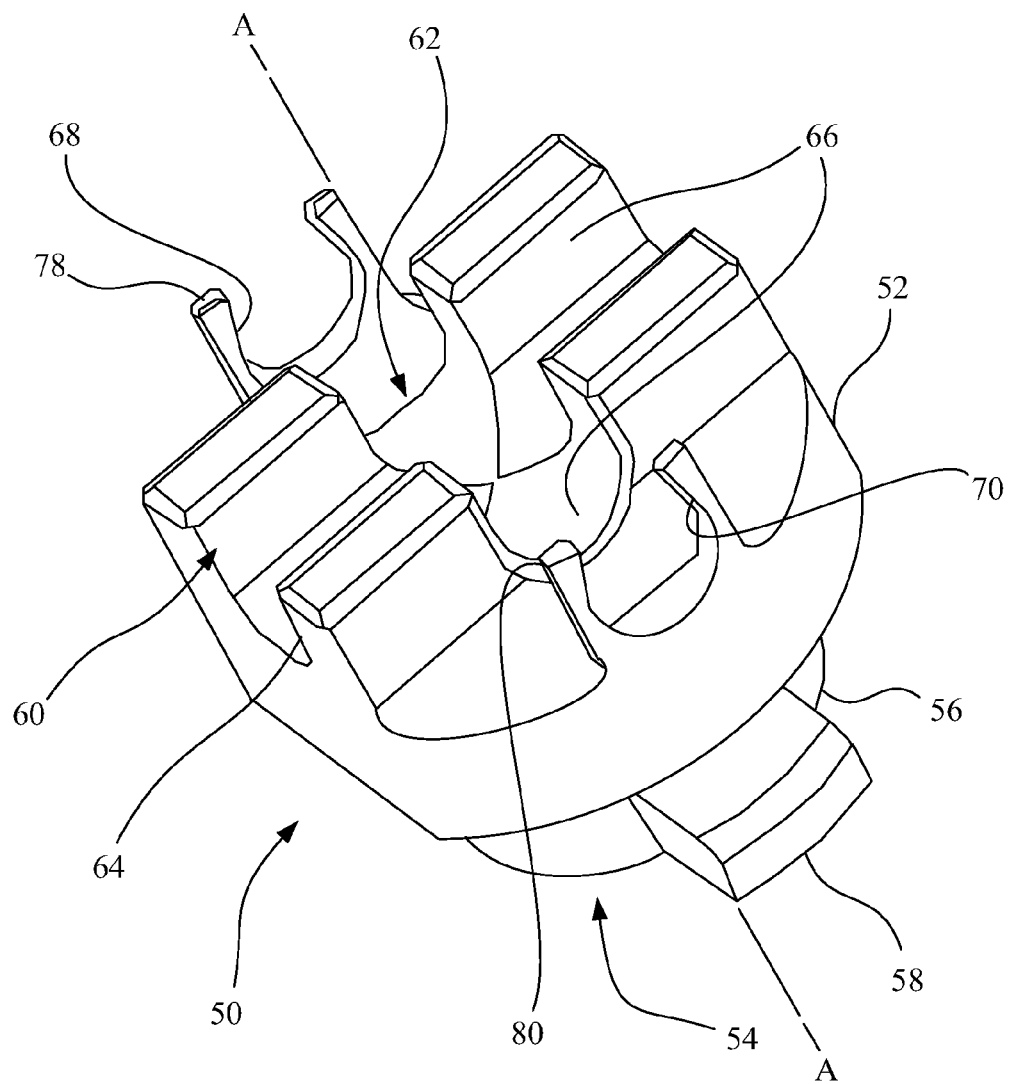
FIG. 3 is a perspective view of an adapter for a crossbar style of reamer.
Figure 4:
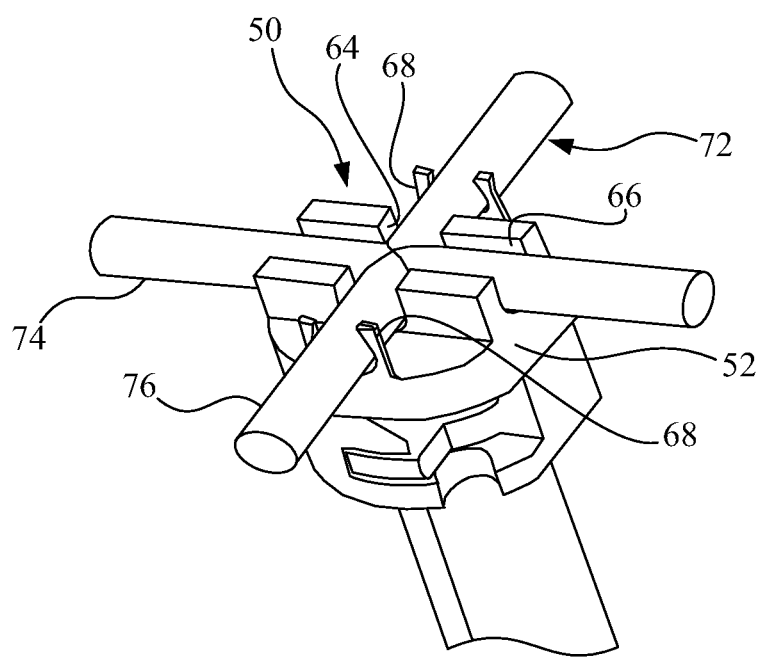
FIG. 4 shows a crossbar reamer in place and in a reamer driver assembly.

Referring now to FIGS. 3 and 4, there is shown an adapter 50 for use in adapting a crossbridge style of reamer driver to a crossbar reamer. Adapter 50 includes a central base 52 having an interface 54 configured to connect with a reamer driver which accepts crossbridge reamers. Interface 54 has a central circular section 56 coaxial with the circular base 52. The diameter of circular section 56 corresponds to the outer diameter of the central circular section of a crossbridge style reamer driver. A pair of opposed radially extending tabs 58 extend from circular center section 56 and duplicate the radially extending tabs of a crossbridge reamer.

The opposite end of circular base 52 has a pair of recesses 60 and 62 configured to receive a crossbar style reamer. Recesses 60 and 62 have semicircular floors 64 and 66, respectively to receive the bars of a crossbar reamer. The recesses 60 and 62 are at right angles with respect to one another so as to match the configuration of the crossbar reamer. In order to releasably hold a crossbar reamer within the grooves 60 and 62, two sets of tabs 68 and 70 are provided. The tabs 68 and 70 extend radially inward just beyond the maximum diameter of a crossbridge reamer so as to hold the crossbar reamer in place.

As shown in FIG. 4, a crossbar reamer 72 is in place in adapter 50 and comprises first and second circular crossbars 74 and 76 positioned at 90° with respect to one another. As such, the bars 74 and 76 are retained within the grooves 60 and 62. As with the crossbridge reamer 34, the bars extend to the interior surface of a semi hemispherical element (not shown) with cutters on it to remove material during a surgical procedure. As shown in FIG. 4, the tabs 68 and 70 resiliently hold the crossbar reamer 72 in place. It should be noted that tabs 68 and 70 have camming surfaces 78 and 80 respectively to permit the tabs 68 and 70 to deform radially outward upon installation of crossbar element 72. As with the adapter 10, adapter 50 is preferably formed from a unitary material compatible with the surgical process, including sterilization. The material used for adapter 50 should have a capability of being resiliently deformed in the area of the tabs for resiliently holding the crossbar adapter.

In both cases, the adapters 10 and 50 permit the removal and installation of the respective reamers in an axial direction so that the additional motion of a bayonet connection can be avoided. This permits removal substantially in an axial direction instead of a combination of axial and rotational movement.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An adapter for surgical reamer driver comprising: a molded unitary piece made from surgically compatible flexible material having a central axis and consisting essentially of:
  a base having an upper surface and an opposing lower surface,
  a plurality of axial recesses formed in said upper surface between axial side walls projecting axially from said upper surface and facing a first direction along the central axis, said recesses having semicircular bases and extending along axes intersecting at the central axis of the unitary piece and perpendicular to one another, wherein said recesses are sized and shaped to match with a configuration of a crossbar reamer;
  a plurality of resilient hook elements projecting in said first direction from the upper surface of said base and located at opposite ends of said base, said plurality of resilient hook elements comprises a pair of opposing resilient hook elements being in line with a pair of opposed axial recesses of the plurality of axial recesses and spaced radially outward from said axial side walls defining the axial recesses, each of said pair of opposing resilient hook elements has a shape which comprises a pair of arms that extends in said first direction from the upper surface of the base and each of said pair of arms terminates in a lip that extends in a direction substantially parallel to the upper surface of the base and substantially perpendicular to said the corresponding arm that extends in the first direction and having a portion with an upper surface at an oblique angle relative to the central axis, wherein the lips of each of the opposing resilient hook elements extend inwardly towards one another for capturing the crossbar reamer, such that when inserting the crossbar reamer axially into the recess, the upper angled surface of the lips allow camming of the opposing lips outwardly by virtue of the yieldability of the hook elements to deflect sufficiently to permit entry of a circular bar of the crossbar reamer and permit the lips to come back into place to securely hold the reamer on the base; and
  a central cylindrical element extending in a second direction along the central axis from the opposing lower surface of the base and being coaxial with said central axis and terminating in an interface, said interface comprising a pair of opposed rectangular elements extending radially outward from the central cylindrical element and being placed in line with one another forming a crossbridge interface configured to connect with a reamer driver that accepts crossbridge style reamers, wherein said adapter enables rapid and immediate connection and disconnection of the crossbar reamer in only an axial direction.

\* \* \* \* \*